United States Patent
Hurry et al.

(10) Patent No.: US 10,102,233 B1
(45) Date of Patent: Oct. 16, 2018

(54) INDEXING FOR DATABASE PRIVACY AND ANONYMIZATION

(71) Applicant: Merck Sharp & Dohme Corp., Rahway, NJ (US)

(72) Inventors: David B. Hurry, Mount Airy, MD (US); David J. Tabacco, Phillipsburg, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/966,927

(22) Filed: Apr. 30, 2018

(51) Int. Cl.
- *G06F 7/00* (2006.01)
- *G06F 17/30* (2006.01)
- *G06F 21/62* (2013.01)
- *G16H 70/60* (2018.01)

(52) U.S. Cl.
CPC ...... *G06F 17/3033* (2013.01); *G06F 21/6254* (2013.01); *G16H 70/60* (2018.01)

(58) Field of Classification Search
CPC .......... G06F 17/30371; G06F 17/3033; G06F 17/30595; G06F 21/6254; G16H 70/60

USPC .................................. 707/747, 754, E17.109
See application file for complete search history.

(56) References Cited

U.S. PATENT DOCUMENTS

2017/0300255 A1* 10/2017 Xu ........................ G06F 3/0619
2018/0137164 A1*  5/2018 Bensberg .......... G06F 17/30498

* cited by examiner

*Primary Examiner* — Md I Uddin
(74) *Attorney, Agent, or Firm* — Fenwick & West LLP

(57) ABSTRACT

An indexing system uses a cascade of hash structures to process data entries upon ingest for indexing. The indexing system may be used for enhancing database privacy, anonymization, or data compression. A hash structure, for example, a bloom filter or hash table, passes a representation of the data entries to a subsequent hash structure in the cascade responsive to determining that the hash structure previously filtered an instance of the same representation. The indexing system can generate the representations of the data entries using one or more hash functions. A terminal hash structure of the cascade may index the data entries responsive to determining that the data entries satisfy a criteria for anonymization. For instance, the indexing system determines that there exists a threshold number of data entries describing a population of subjects having the same combination of data elements.

15 Claims, 10 Drawing Sheets

| Data Entry | Status | Date |
|---|---|---|
| USER:10000_ZIP:08854 | Cleared Hash Structure 1 | 1/27/17 |
| USER:10000_ZIP:08854 | Cleared Hash Structure 2 | 1/27/17 |
| USER:10000_ZIP:08854 | Stored in Hash Structure 3 | 1/27/17 |
| USER:10001_ZIP:12853 | Cleared Hash Structure 1 | 1/27/17 |
| USER:10001_ZIP:12853 | Stored in Hash Structure 2 | 1/27/17 |
| USER:10002_ZIP:08876 | Cleared Hash Structure 1 | 1/28/17 |
| USER:10002_ZIP:08876 | Cleared Hash Structure 2 | 1/28/17 |
| USER:10002_ZIP:08876 | Cleared Hash Structure 3 | 1/28/17 |
| USER:10002_ZIP:08876 | Cleared Hash Structure 4 | 1/28/17 |
| USER:10002_ZIP:08876 | Indexed in Database | 1/28/17 |
| USER:10000_SEX:M | Cleared Hash Structure 1 | 1/27/17 |
| USER:10000_SEX:M | Cleared Hash Structure 2 | 1/27/17 |
| USER:10000_SEX:M | Stored in Hash Structure 3 | 1/27/17 |
| USER:10001_SEX:F | Cleared Hash Structure 1 | 1/27/17 |
| USER:10001_SEX:F | Cleared Hash Structure 2 | 1/27/17 |
| USER:10001_SEX:F | Cleared Hash Structure 3 | 1/27/17 |
| USER:10001_SEX:F | Cleared Hash Structure 4 | 1/27/17 |
| USER:10001_SEX:F | Indexed in Database | 1/27/17 |
| USER:10002_SEX:M | Stored in Hash Structure 3 | 1/27/17 |
| USER:10002_SEX:M | Cleared Hash Structure 1 | 1/27/17 |
| USER:10002_SEX:M | Cleared Hash Structure 2 | 1/27/17 |
| USER:10002_SEX:M | Cleared Hash Structure 3 | 1/27/17 |
| USER:10002_SEX:M | Stored in Hash Structure 4 | 1/27/17 |

INDEXING FOR DATABASE PRIVACY AND ANONYMIZATION

TECHNICAL FIELD

The disclosure is related to the field of database indexing and to hash data structures.

BACKGROUND

Existing database systems may use rules for indexing data entries into databases. For example, the rules are used for protecting sensitive data. If a data entry satisfies a rule, the system may determine to index the data entry. However, by determining whether the data entry satisfies the rule, the database system can expose sensitive content of the data entry. The technical challenges of indexing and anonymizing data across sources are barriers to efficient data management operations and broader discovery of new research opportunities.

BRIEF DESCRIPTION OF THE DRAWINGS

The disclosed embodiments have advantages and features which will be more readily apparent from the detailed description, the appended claims, and the accompanying figures (or drawings). A brief introduction of the figures is below.

FIG. 3E is a partial log of data entries processed by the example cascade of hash structures shown in FIG. 3A in accordance with one embodiment.

DETAILED DESCRIPTION

Figure 1:
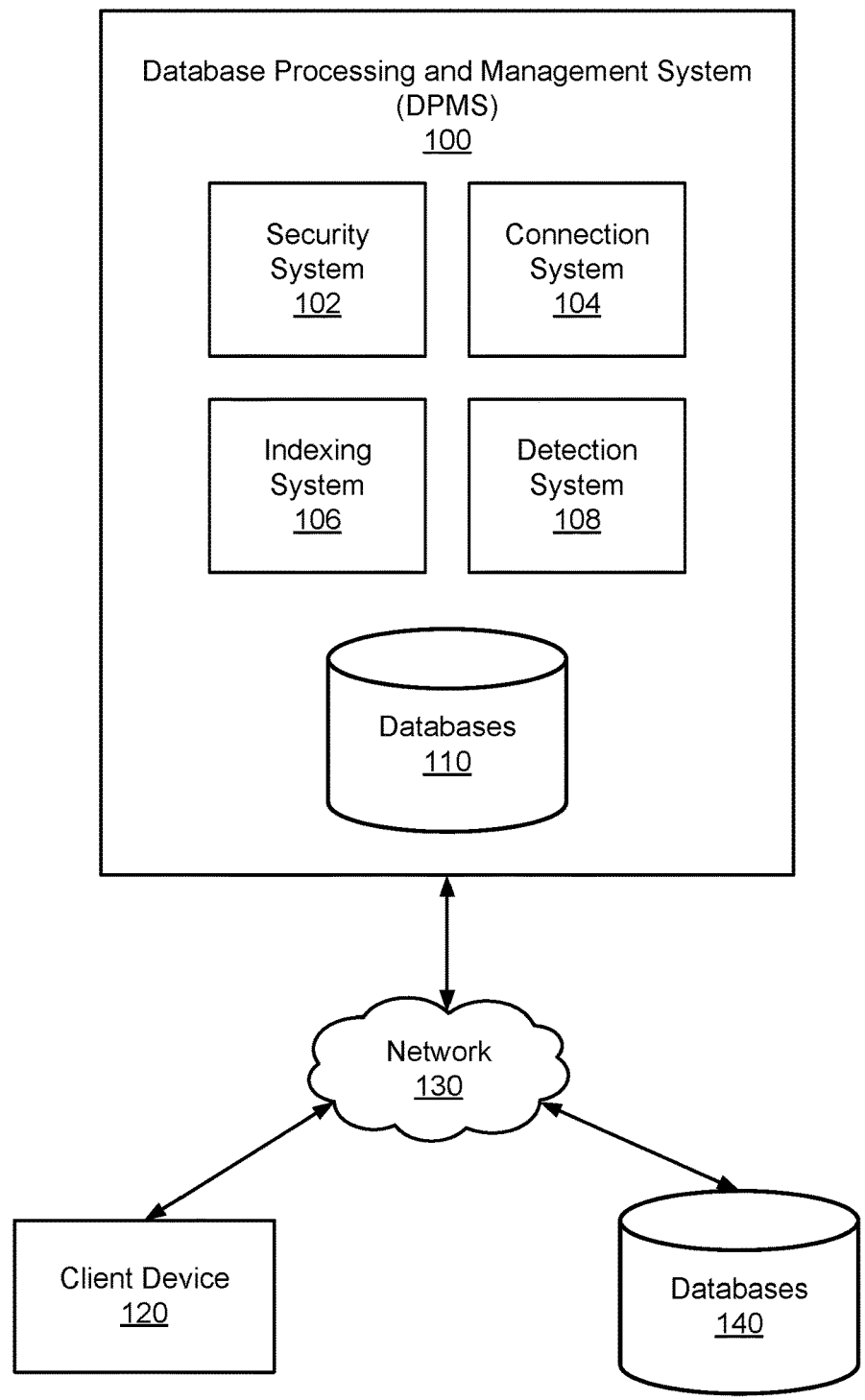
FIG. 1 illustrates an example system environment for a database processing and management system (DPMS) in accordance with one embodiment.

The Figures (FIGS.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Configuration Overview

An indexing system may provide database privacy by enhancing anonymization of data entries. For example, sensitive data entries to be anonymized may indicate a subject's geographical location or other identifying information. The indexing system uses an intentionally lossy compression model that indexes one or more data entries responsive to determining that the one or more data entries can be anonymized with a set of other data entries. The indexing system may generate a representation (e.g., a hash representation) of data entries to input to the model. In some embodiments, the model includes a cascade of hash structures to process data entries upon ingest to the indexing system. A hash structure passes the representation of the data entries to a subsequent hash structure in the cascade responsive to determining that the hash structure previously filtered an instance of the same representation. A terminal hash structure of the cascade may index the data entries responsive to determining that the data entries satisfy a criteria for anonymization. For instance, the indexing system determines that there exists a threshold number of data entries describing a population of subjects having the same geographical location and disease diagnosis. Thus, each individual subject of the population cannot be uniquely identified (e.g., by a data element pair) from the other subjects.

The disclosed embodiments of the indexing system provide a technical solution to a challenge unique to computing environments for database indexing and anonymization. Existing systems face technical issues in attempting to anonymize sensitive information. For example, an administrator wants to create a database of subjects located in a particular geographical location that have been diagnosed with a certain disease. Additionally, the administrator wants to anonymize the data entries such that the identity of a specific subject cannot be determined from the database. The administrator may count data entries of subjects upon ingest and choose to index once a predetermined number of data entries have been checked. However, to check whether a data entry is associated with the geographical location and disease of interest, existing systems may inadvertently expose the sensitive data. The technical solution disclosed herein addresses these and other issues by providing an indexing algorithm that determines whether to filter or pass representations of data entries through a cascade of hash structures. The indexing system may use the indexing algorithm for enhancing database privacy, anonymization, data compression, or other suitable applications related to database processing.

System Overview

FIG. 1 illustrates an example system environment for a database processing and management system (DPMS) in accordance with one embodiment. The system environment shown in FIG. 1 includes the DPMS 100, client device 120, and one or more databases 140, which are connected to each other via a network 130. In other embodiments, different or additional entities can be included in the system environment. For example, though only one client device 120 and database 140 is shown in FIG. 1, the system environment may include additional client devices 120 and/or databases 140. The functions performed by the various entities of FIG. 1 may vary in different embodiments.

The DPMS 100 includes a security system 102, connection system 104, indexing system 106, detection system 108, and one or more databases 110. Alternative embodiments may include different or additional modules or omit one or more of the illustrated modules. The indexing system 106 indexes data entries for storage in databases and processes queries for data entries from the databases. The indexing system 106 is further described below with reference to FIGS. 2-5.

Data entries may be stored in one or more of the databases 110 of the DPMS 100 or stored in other databases (e.g., databases 140) or systems outside of the DPMS 100. The embodiments herein describe data entries that may represent discrete events of a subject such as a medical symptom, diagnosis, treatment, procedure, gene expression, etc. In some embodiments, data entries may include various types of information including, for example, experimental data (e.g., molecular compounds, lab procedures, or scientific findings), intellectual property (e.g., patents or trade secrets), contracts (e.g., terms of use for licensed data), regulatory requirements (e.g., for scientific and financial filings with a government organization), sensitive information (e.g., patient information, health records, or human resources data), information technology controls (e.g., usernames, passwords, or other security credentials), among other types of information. A data entry may have any suitable format for representing discrete or continuous data, for example, an integer, decimal value, Boolean, string, character, timestamp, etc.

In some embodiments, the indexing system 106 may operate in conjunction with one or more other subsystems of the DPMS 100. The security system 102 determines and updates authorizations for users to perform various types of interactions with data entries of the DPMS 100. The connection system 104 determines connections between the data entries. In one use case, responsive to determining that multiple databases include related information (e.g., data from a hospital, a government agency, or a third party system), the connection system 104 may join or generate a union between data entries stored in the databases, e.g., 110, 140. The detection system 108 may classify the data entries. In some embodiments, the detection system 108 assumes that the data entries are self-expressive and determines the classifications based on contents of the data entries, e.g., rather than on labels of the data entries because the labels may vary between data sources from different systems.

Each client device 120 comprises one or more computing devices capable of processing data as well as transmitting and receiving data over a network 130. For example, a client device 120 may be a desktop computer, a laptop computer, a mobile phone, a tablet computing device, an Internet of Things (IoT) device, or any other device having computing and data communication capabilities. Each client device 120 includes a processor for manipulating and processing data, a network connection for communicating with other devices, and a storage medium for storing data, program code, and/or program instructions associated with various applications. It is noted that a storage medium may include volatile memory (e.g., random access memory) and/or non-volatile storage memory such as hard disks, flash memory, and external memory storage devices.

The network 130 may comprise any combination of local area and wide area networks employing wired or wireless communication links. In one embodiment, network 130 uses standard communications technologies and protocols. For example, network 130 includes communication links using technologies such as Ethernet, 802.11, worldwide interoperability for microwave access (WiMAX), 3G, 4G, 5G, code division multiple access (CDMA), digital subscriber line (DSL), etc. Examples of networking protocols used for communicating via the network 130 include multiprotocol label switching (MPLS), transmission control/protocol/Internet protocol (TCP/IP), hypertext transport protocol (HTTP), simple mail transfer protocol (SMTP), and file transfer protocol (FTP). Data exchanged over the network 130 may be represented using any format, such as hypertext markup language (HTML) or extensible markup language (XML). In some embodiments, all or some of the communication links of the network 130 may be encrypted.

Example System Architecture

Figure 2:
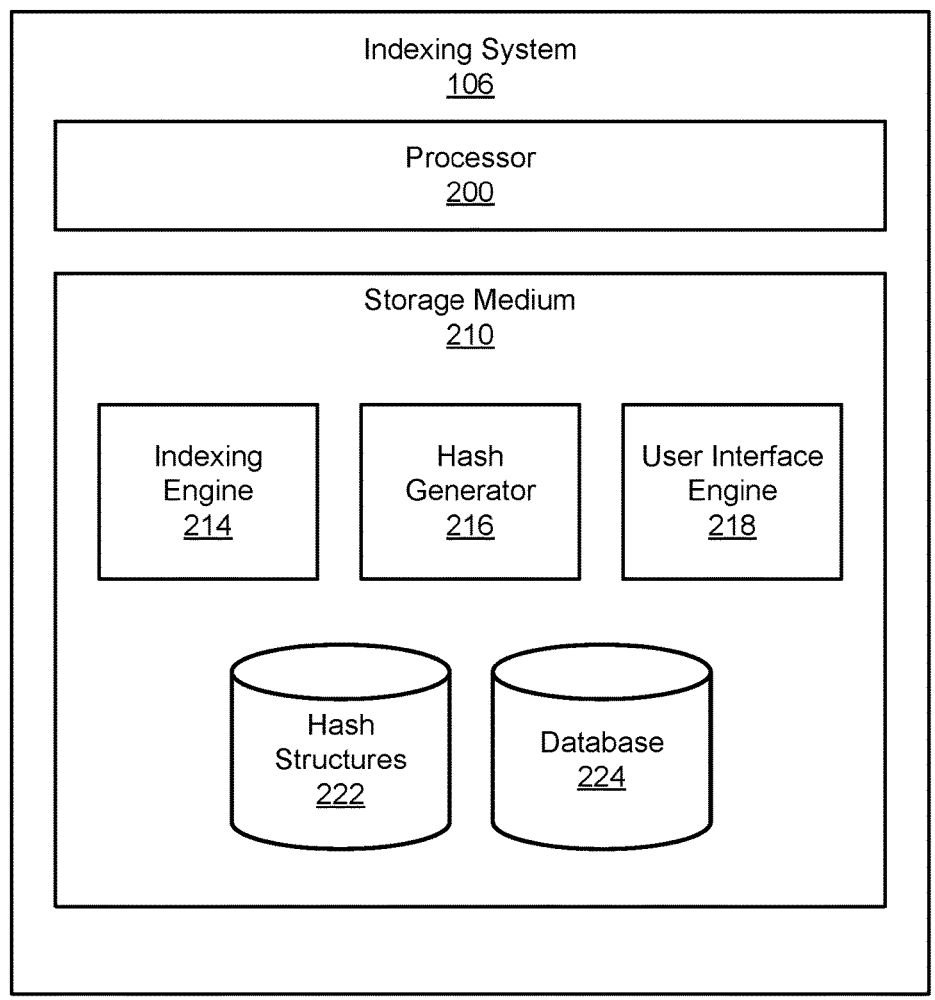
FIG. 2 illustrates an example block diagram of an indexing system in accordance with one embodiment.

FIG. 2 illustrates an example block diagram of the indexing system 106 in accordance with one example embodiment. The indexing system 106 may include a processor 200 for manipulating and processing data, a network connection for communicating with other devices, and a storage medium 210 for storing data and program instructions associated with various modules. In one example embodiment, the storage medium 210 comprises a non-transitory computer-readable storage medium. Various executable programs are each embodied as computer-executable instructions stored to the non-transitory computer-readable storage medium 210. The instructions when executed by the processor 200 cause the indexing system 106 to perform the functions attributed to the programs described herein. Further detail of an example computer system corresponding to the indexing system 106 is described below with reference to FIG. 6. The storage medium 210 includes an indexing engine 214, hash generator 216, user interface engine 218, hash structures 222, and one or more databases 224. Alternative embodiments may include different or additional modules or omit one or more of the illustrated modules.

The indexing engine 214 receives data entries for indexing in one or more of the databases 224 of the indexing system 106, databases 110 of the DPMS 100, or other databases 140 connected to the DPMS 100. The indexing engine 214 may use an intentionally lossy model to determine whether or not to index the data entries. Moreover, the indexing engine 214 may use the model for database privacy by enhancing anonymization or for data compression. The model includes a cascade or series of multiple hash structures 222. Generally, a hash structure 222 is a data structure that implements a hash function to map keys to values of a dataset. Example hash structures 222 include bloom filters or hash tables.

A bloom filter may be applied to determine whether an element is not in a set of elements or potentially in the set of elements. Stated differently, the bloom filter may return false positives but not false negatives regarding matching (e.g., mapping) elements to the set. In an embodiment, the element is a representation of data entries, e.g., a hash representation or a relative attribute of at least a portion of the data entries. The set of elements includes representations previously seen by (e.g., input to) the bloom filter. The bloom filter may determine to filter out representations that have not been previously seen by the bloom filter and pass (e.g., not filter) representations that have been previously seen by the bloom filter. By using a cascade of a number of bloom filters that determine whether to filter or pass representations of data entries to subsequent bloom filters in the cascade, the indexing system 106 may help improve anonymization of the data entries by ensuring that the model has seen a threshold number of instances of a given representation or set of data entries. As an example, the threshold number may be eleven, which is implemented by a cascade of eleven bloom filters. However, in other embodiments, the cascade may have at least a different threshold number of hash structures. Since the bloom filters process representations of data entries and not the data entries themselves, the indexing engine 214 can also prevent unwanted exposure of sensitive or confidential content of the data entries.

A bloom filter may include a fixed size to map an arbitrary number of elements. As the number of elements processed by the bloom filter increases, the false positive rate may also increase due to the greater likelihood of a collision in the hash function. In some embodiments, the indexing engine 214 tracks a count of data entries added to a bloom filter. Responsive to determining that the count reaches a threshold count, the indexing engine 214 may start or use an additional bloom filter to reduce the probability of collisions. In other embodiments, the indexing engine 214 uses a different type of hash structure, e.g., a hash table, which does not have a fixed size. In particular, a hash table may be dynamically resized as the number of processed elements increases.

The hash generator 216 generates hash representations of data entries using one or more hash functions. A hash function may be a one-way function such that sensitive content of data entries cannot be identified using the output hash representation, thus enhancing protection of privacy of the sensitive content during processing by the indexing system 106. The indexing engine 214 may transmit the hash representations to the hash structures 222 for filtering.

In some example embodiments, the indexing engine 214 receives a selection of data elements of one or more data entries for indexing. The hash generator 216 generates hash representations of the data entries using at least the selected data elements. As an example use case, the data entries describe attributes of a subject and indicate demographics (e.g., age, gender, ethnicity, etc.), geographical location (e.g., city, state, zip code, neighborhood, etc.), diagnosed disease, health conditions, or medical procedure. A user or administrator of the indexing system 106 may input the selection based on target information of interest. For instance, the user wants to anonymize information from a population of subjects based on diagnosed disease and geographical location, or a certain type of one or more events. As the selectivity of data elements increases, the number of instances required to be processed by a cascade of hash structures 222 before indexing may decrease. In other words, without a selection of certain data elements, there may be a large amount of variability in the data entries, which reduces the likelihood of a given representation of data entries being passed through the cascade (e.g., lower rate of collisions/matches in the hash structures). In some embodiments, the hash structures may save space by not requiring inverted indexes.

The user interface engine 218 generates user interface layouts and provides the user interface layouts to client devices 120. Users may use the client devices 120 to interact with the indexing system 106 via the user interface layouts. For instance, a user may select data entries for indexing, anonymization, or compression by the indexing system 106. As an example use case, the user interface engine 218 generates a user interface layout for a user to select data elements of data entries for the indexing system 106 to process. In other use cases, a user may query databases or query for indexed data entries using a user interface of a client device 120.

Example Hash Structures

An example use case of anonymizing data entries using a cascade of hash structures 222 is described below with references to FIGS. 3A-C. The example cascade shown in the figures includes at least four hash structures, though it should be noted that in other embodiments, a cascade may include any number of hash structures 222.

Figure 3A:
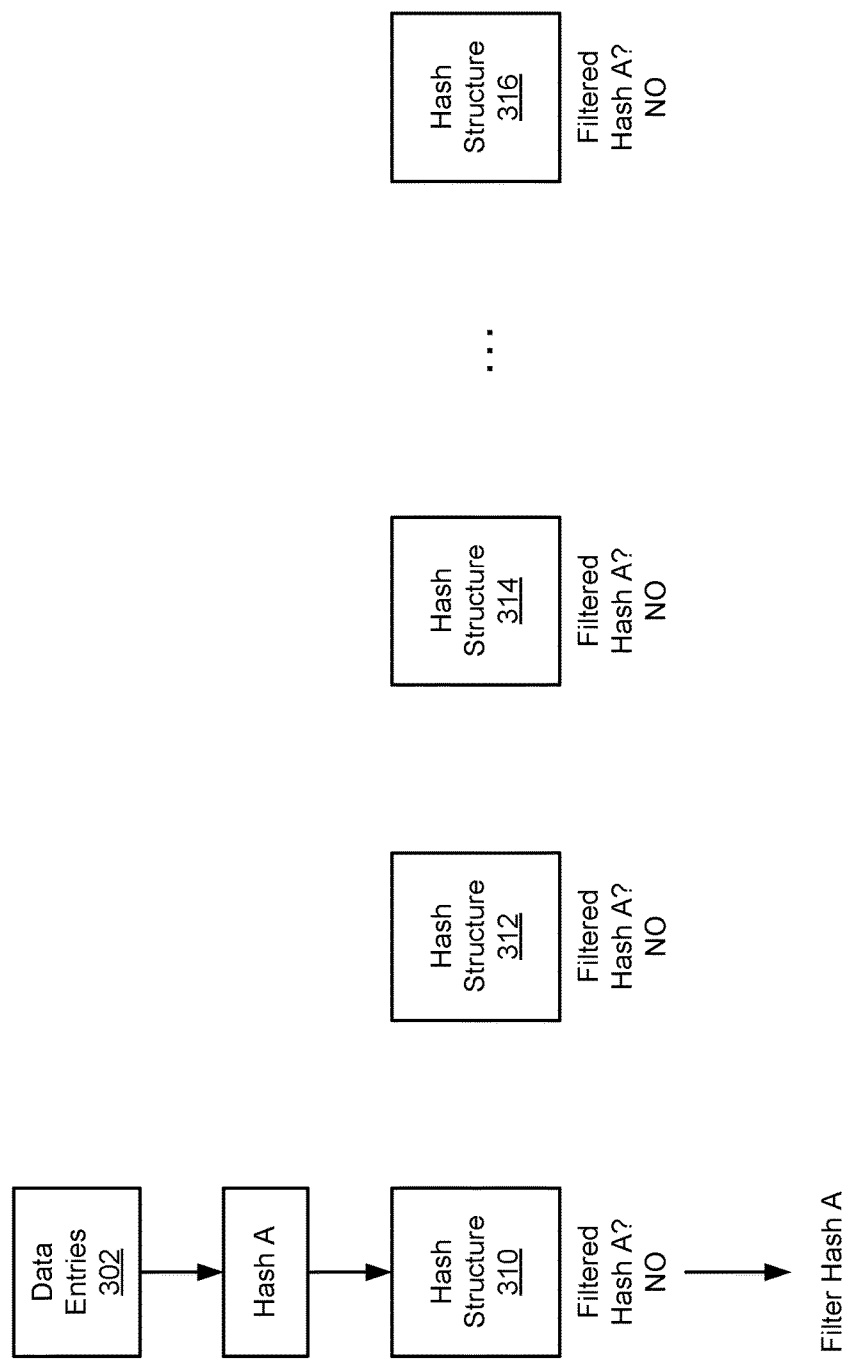
FIG. 3A illustrates a diagram of an example cascade of hash structures in accordance with one embodiment.

FIG. 3A illustrates a diagram of an example cascade of hash structures in accordance with one embodiment. The indexing system 106 receives data entries 302 to be potentially indexed into a database. The hash generator 216 generates a hash representation Hash A of the data entries 302. The indexing engine 214 provides Hash A to a cascade of hash structures. The first hash structure 310 of the cascade determines if it has filtered (e.g., previously seen) Hash A. In an embodiment, the hash structures each include an array of n bits, where n is an integer value. Initially, the arrays of the hash structures are empty and thus have not filtered Hash A because the indexing system 106 has not yet received data entries for indexing. Over time, the hash structures test hash representations of data entries, and the hash structures map the hash representations to positions in the arrays.

Responsive to determining that the hash structure 310 has not filtered Hash A, the hash structure 310 filters Hash A and maps Hash A to a position in the corresponding array of hash structure 310. The indexing system 106 determines not to index the data entries 302 responsive to determining that hash structure 310 filtered Hash A. Accordingly, the indexing system 106 does not index the data entries 302 because the indexing system 106 cannot anonymize the data entries 302 based on the data entries received so far by the indexing system 106.

Figure 3B:
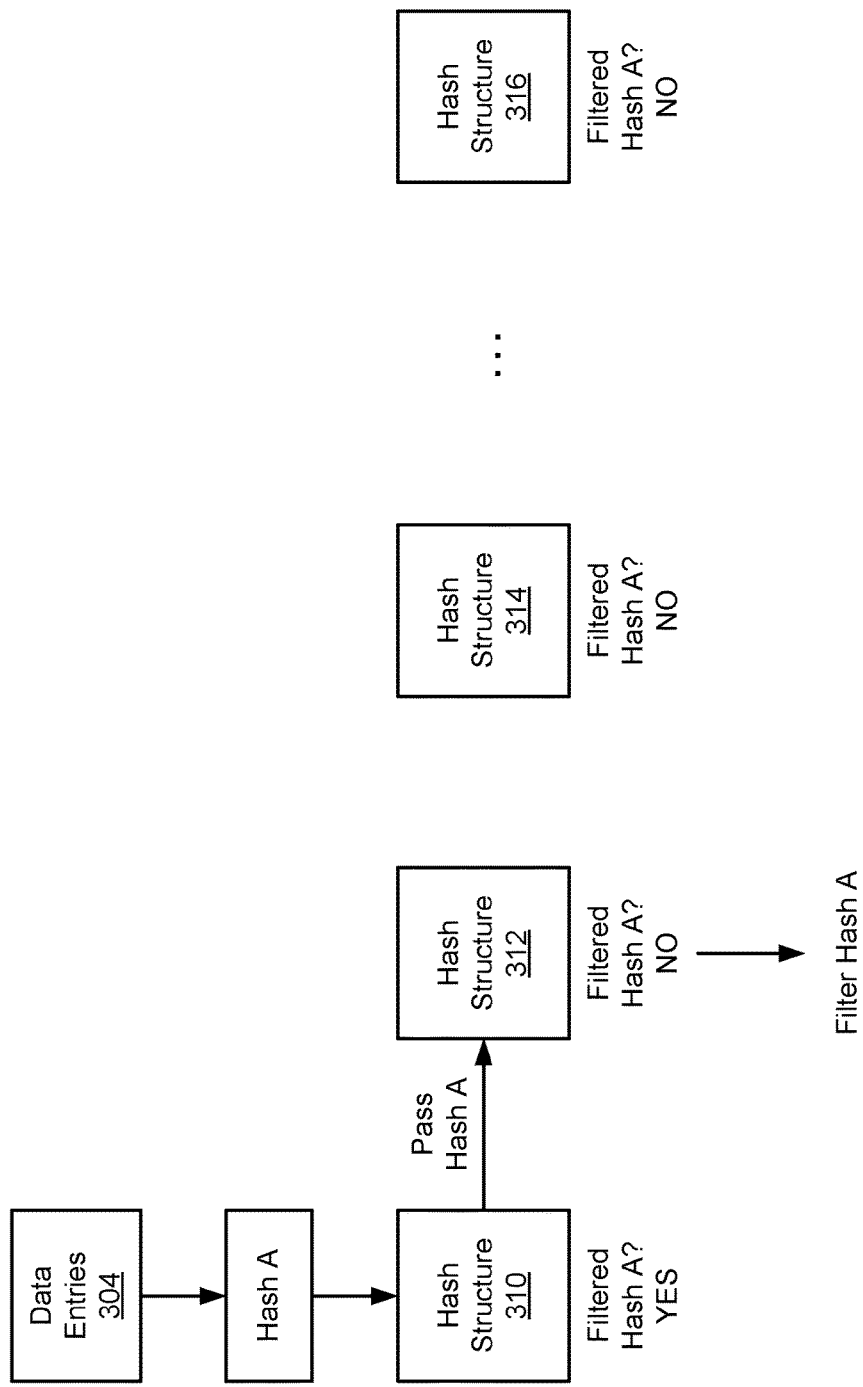
FIG. 3B illustrates another diagram of the example cascade of hash structures shown in FIG. 3A in accordance with one embodiment.

FIG. 3B illustrates another diagram of the example cascade of hash structures shown in FIG. 3A in accordance with one embodiment. Following in the same example shown in FIG. 3A, the indexing system 106 receives data entries 304 to be potentially indexed into the database. The hash generator 216 generates the hash representation Hash A of the data entries 304. The indexing engine 214 provides Hash A to a cascade of hash structures. Hash A may be the same hash representation for data entries 302 (shown in FIG. 3A) and 304, which indicates that data entries 302 and 304 may have the same or similar content. Responsive to determining that hash structure 310 filtered Hash A of data entries 302, the hash structure 310 determines to pass Hash A of data entries 304 to a subsequent hash structure 312 in the cascade.

Hash structure 312 receives the passed Hash A from hash structure 310. Responsive to determining that hash structure 312 has not filtered Hash A, the hash structure 312 determines to filter Hash A. Thus, the indexing system 106 does not index the data entries 304 because the indexing system 106 cannot anonymize the data entries 304 based on the data entries received thus far by the indexing system 106 (e.g., data entries 302 and 304). The indexing system 106 may repeat the process shown in FIGS. 3A-B any number of times to process additional data entries, and the hash structures may "absorb" the data entries by mapping hash representations of the additional data entries to positions of the corresponding arrays of the hash structures.

Figure 3C:
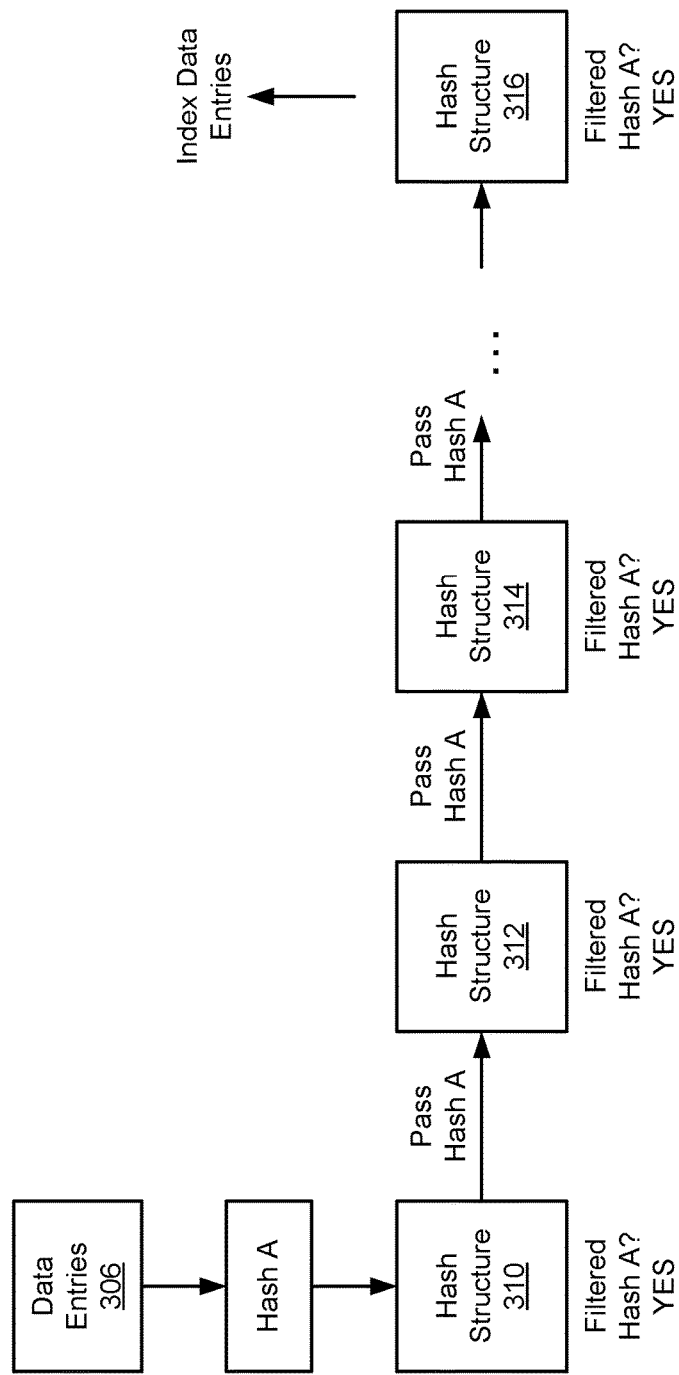
FIG. 3C illustrates yet another diagram of the example cascade of hash structures shown in FIG. 3A in accordance with one embodiment.

FIG. 3C illustrates yet another diagram of the example cascade of hash structures shown in FIG. 3A in accordance with one embodiment. Following in the same example shown in FIG. 3A-B, after the indexing system 106 processes multiple data entries, the cascade model reaches a state where each hash structure of the cascade has filtered Hash A. The indexing system 106 receives data entries 306 to be potentially indexed into the database. The hash generator 216 generates the hash representation Hash A of the data entries 306. The indexing engine 214 provides Hash A to the cascade of hash structures. Hash A may be the same hash representation for data entries 302 (shown in FIG. 3A), 304 (shown in FIG. 3B), and 306.

Since the hash structures 310, 312, and 314 shown in FIG. 3C as well as any other subsequent hash structures in the cascade have filtered Hash A, the hash structures pass Hash A to a terminal hash structure 316. Responsive to determining that hash structure 316 filtered Hash A of data entries 306, the hash structure 316 determines to index data entries 304. At this point, the indexing system 106 has processed a threshold amount of data entries (e.g., at least data entries 302, 304, and 306), and thus satisfies a criteria for anonymization of the content of data entries 306. For example, content of data entries 306 cannot be directly or uniquely identified from content aggregated from the other data entries, including at least data entries 302 and 304. Additionally, the indexing system 106 may have also compressed data entries 302, 304, and 306 for storage in the database. In particular, the cascade of hash structures absorbed the processed data entries, which may result in noise reduction because "long tail" statistical events are filtered out. For example, the long tail events represent instances of data that are sufficiently infrequent or low-amplitude in a dataset, e.g., which makes them statistically insignificant as to be useful for analytic use.

Figure 3D:
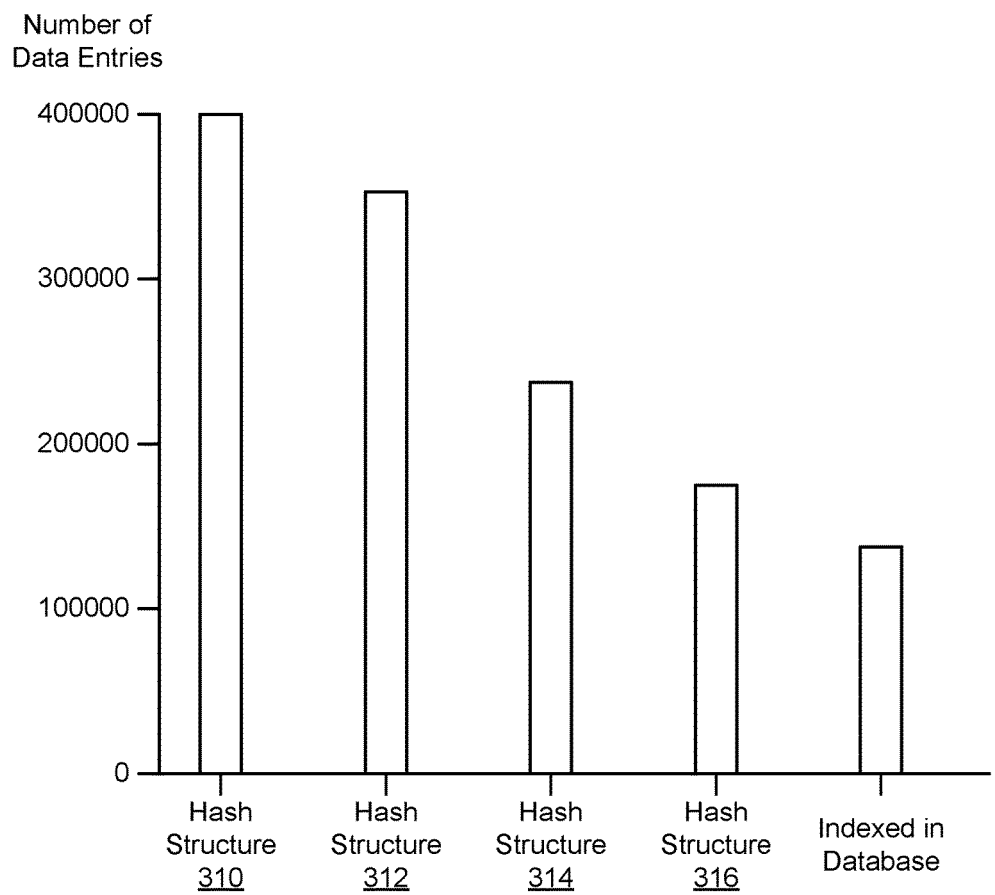
FIG. 3D is a table showing counts of data entries processed by the example cascade of hash structures shown in FIG. 3A in accordance with one embodiment.

FIG. 3D is a table showing counts of data entries processed by the example cascade of hash structures shown in FIG. 3A in accordance with one embodiment. The table illustrates that the counts of data entries passed may generally decrease as the data entries progress through the cascade, e.g., hash structures 310, 312, 314, and 316. Moreover, the count of data entries indexed by the indexing engine 214 is a fraction of a total count of data entries ingested by the indexing engine 214. The magnitudes of change in counts of data entries passed may vary between hash structures. For instance, the decrease in data entries from hash structure 312 to hash structure 314 is the greatest among the changes shown in the embodiment of FIG. 3D.

FIG. 3E is a partial log of data entries processed by the example cascade of hash structures shown in FIG. 3A in accordance with one embodiment. The hash structures 310, 312, 314, and 316 shown in FIGS. 3A-D may correspond to the example hash structures 1, 2, 3, and 4 shown in FIG. 3E, respectively. The partial log shown in FIG. 3E may be a portion of a complete log. For instance, the partial log begins at an intermediate point in processing where prior data entries have previously been ingested by the cascade of hash structures. The log includes data elements (e.g., user identifiers, zip code, and gender), statuses, and a date (e.g., as a timestamp). The status indicates whether a given data entry was cleared or stored (e.g., mapped) by one of the hash structures, or indexed in a database by the indexing engine 214.

Figure 4:
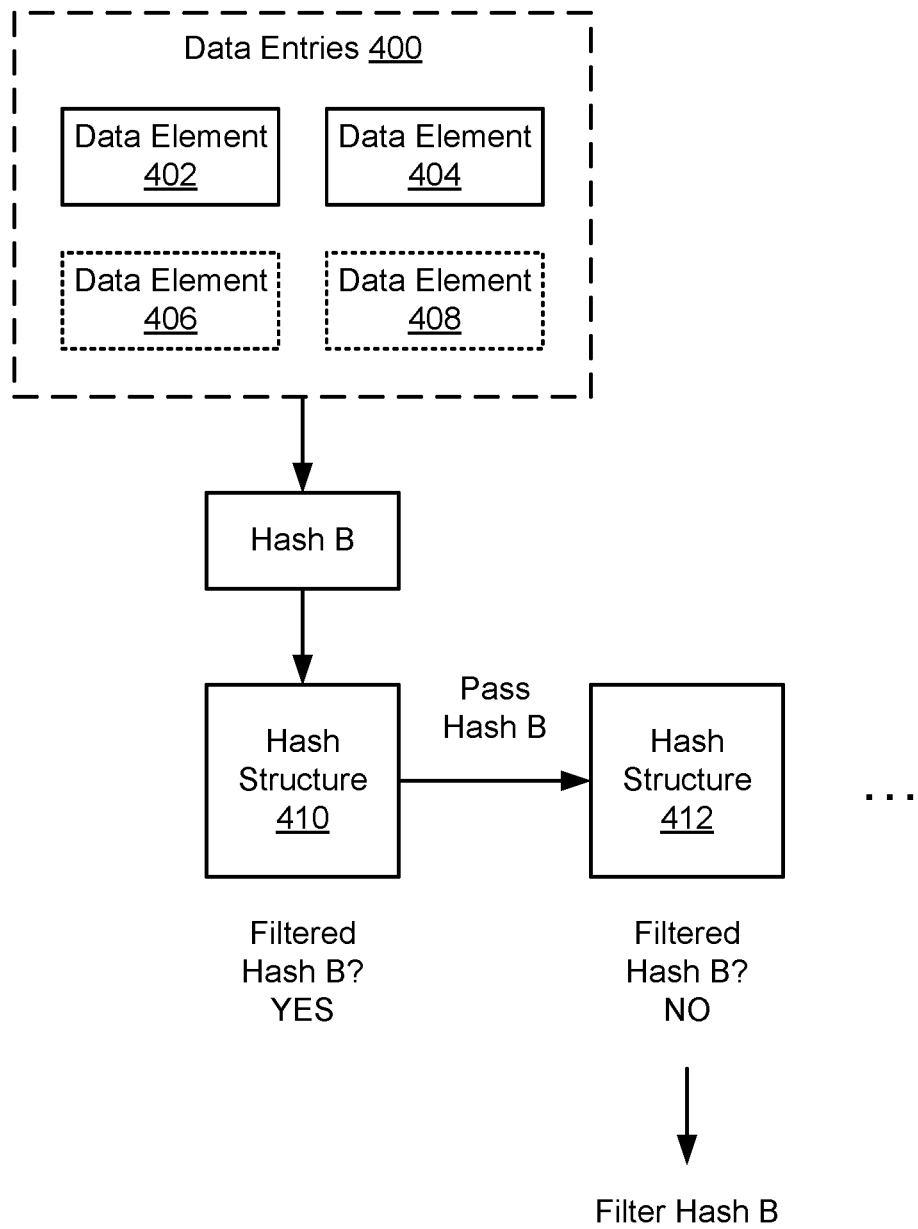
FIG. 4 illustrates an example input to a cascade of hash structures in accordance with one embodiment.

FIG. 4 illustrates an example input to a cascade of hash structures in accordance with one embodiment. The indexing engine 214 receives data entries 400 including at least data elements 402, 404, 406, and 408. In addition, the indexing engine 214 receives a selection of data elements 402 and 404 for indexing the data entries 400. As an example use case, the data elements describe attributes of a subject. For instance, the data elements 402 and 404 indicate a geographical location and a diagnosed disease of the subject, respectively. Other example data elements may indicate an age or gender of the subject. The hash generator 216 generates the hash representation Hash B of the data entries 400 using the data elements 402 and 404. In particular, the hash generator 216 may apply a hash function to values of the selected data elements and not to unselected data elements. Accordingly, the Hash B value may vary based on which data elements are selected by a user.

In some embodiments, the data elements describe events of a subject, e.g., a medical symptom, diagnosis, treatment, or procedure, associated with a timestamp. The hash generator 216 may determine a relative attribute between the data elements. For example, the hash generator 216 determines a temporal distance between timestamps of the data elements 402 and 404, indicating a duration of time from an observed symptom to a disease diagnosis of the subject. The hash generator 216 may generate a hash representation using one or more relative attributes of data elements. Relative attributes may be based on absolute time, reference time (e.g., day of the week or hour of the day), physical proximity, altitude, semantics, etc.

Following in the above example, the indexing engine 214 provides Hash B to the hash structure 410 of a cascade. Responsive to determining that hash structure 410 filtered Hash B of data entries 400, the hash structure 410 determines to pass Hash B to a subsequent hash structure 412 in the cascade. Responsive to determining that hash structure 412 has not filtered Hash B, the hash structure 412 determines to filter Hash B. Given the current state of the cascade, the indexing engine 214 does not index the data entries 400 because the indexing engine 214 has not yet satisfied a criteria for anonymizing the data entries 400, e.g., based on the selected data elements 402 and 404.

In some embodiments, the indexing engine 214 may index portions of a data entry that satisfy a privacy criteria even though the data entry as a whole may not necessarily satisfy the privacy criteria. For example, the data entries may include data elements describing a user's name, geographical location, gender, and age. Each hash structure of a cascade may determine to pass the data entries when hashing a subset of the data elements, e.g., the indexing engine 214 is able to anonymize based on name and geographical location. However, the indexing engine 214 may not necessarily be able to anonymize based on gender or age (e.g., at a given point in time using an initial set of data entries). Accordingly, the indexing engine 214 may determine to index the name and geographical location information of users but to not index the gender or age information of the users, e.g., until further data entries are processed that satisfy a criteria for protection of the gender or age information.

Example Process Flow

Figure 5:
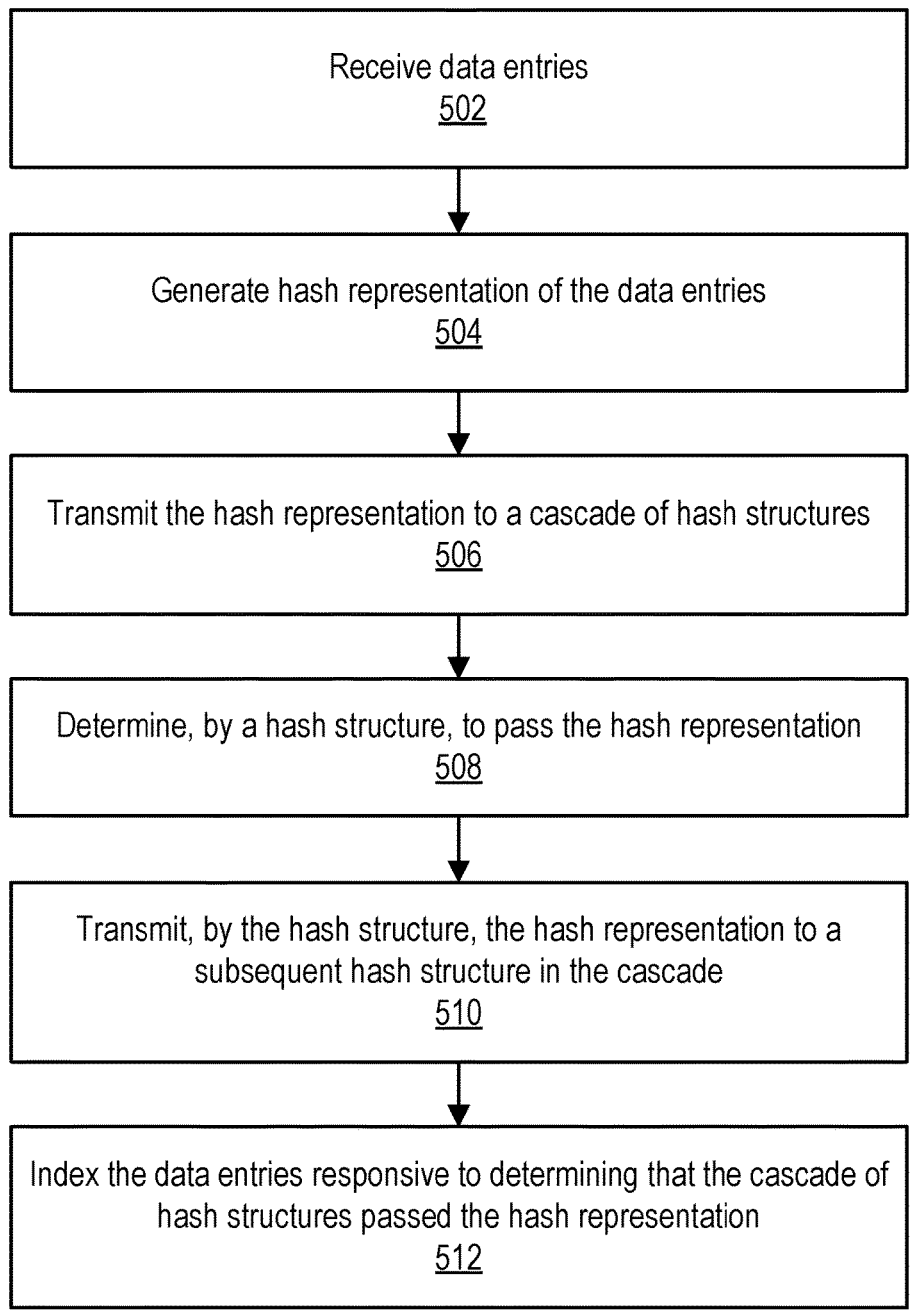
FIG. 5 illustrates an example process flow for anonymizing data entries in accordance with one embodiment.

FIG. 5 illustrates an example process flow 500 for anonymizing data entries in accordance with one embodiment. The process 500 may include different or additional steps than those described in conjunction with FIG. 5 in some embodiments or perform steps in different orders than the order described in conjunction with FIG. 5. The indexing engine 214 of the indexing system 106 receives 502 data entries for indexing in a database. The hash generator 216 generates 504 a hash representation of the data entries. In some embodiments, the indexing engine 214 receives the hash representation, which may be predetermined or generated by a source external to the indexing system 106. In some embodiments, the indexing engine 214 receives, from a client device 120 of a user, a selection of multiple data elements (e.g., a subset) of the data entries. The hash generator 216 may generate the hash representation using the selected data elements.

The indexing engine 214 transmits 506 the hash representation to a cascade of hash structures 222 of the indexing system 106. At least one of the hash structures 222 is configured to determine 508 to pass the hash representation responsive to determining that the hash structure previously filtered another instance of the hash representation. The hash structure is further configured to transmit 510 the hash representation to a subsequent hash structure in the cascade responsive to the determination to pass the hash representation. The indexing engine 214 indexes 512 the data entries into the database responsive to determining that each hash structure of the cascade determined to pass the hash representation. The indexing engine 214 may transmit a notification to a client device 120 indicating that the data entries have been indexed into the database.

In an embodiment, the indexing engine 214 generates or receives another hash representation of another set of data entries (e.g., different than the hash representation that was passed as described above). The indexing engine 214 transmits the other hash representation to the cascade of hash structures. The indexing engine 214 determines not to index the other set of data entries responsive to determining that one of the hash structures of the cascade does not pass the other hash representation. For instance, the indexing engine 214 has not yet satisfied a criteria for anonymization of the other set of data entries based on the hash representations filtered so far by the hash structures. In some embodiments, the data entries that are not passed by the hash structures may be recovered in an emergency protocol. For example, in addition to generating hash representation of data entries, the hash generator 216 may also store the data entries in a buffer secured using encryption. In some embodiments, the hash generator 216 encrypts the data entries using a public key provided by a third party. Further, the data entries may be stored on the DPMS 100 or on another system, which may be associated with the third party. As an example use case, the indexing system 106 is used for protecting user information for a clinical trial. Responsive to a user-specific or patient-specific event, e.g., during or after the clinical trial, the indexing system 106 may recover data entries from the secured buffer though a third party or by the holder of the associated private key.

Physical Components

Figure 6:
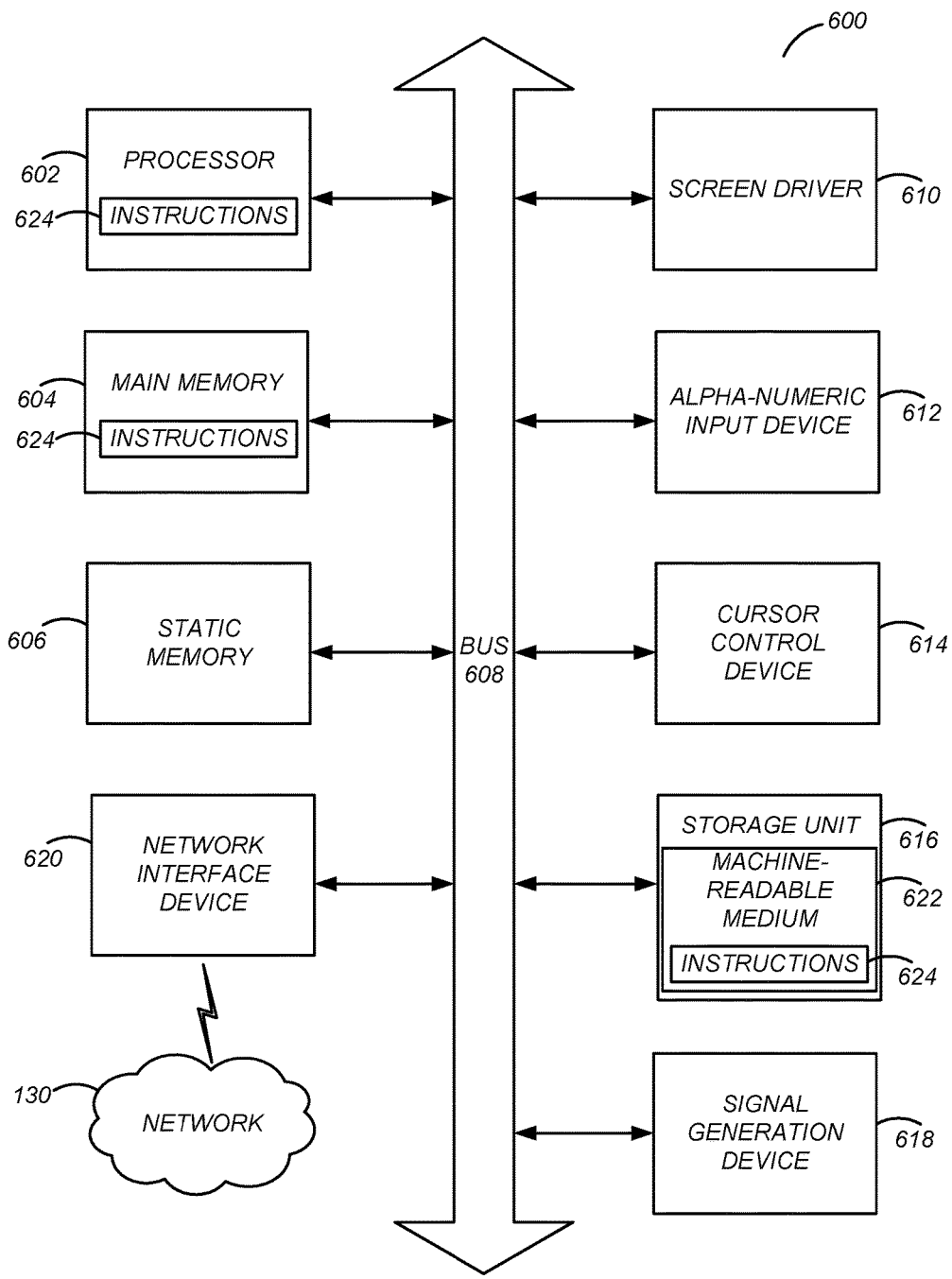
FIG. 6 is a block diagram illustrating components of an example machine able to read instructions from a machine-readable medium and execute them in one or more processors (or controllers) in accordance with one embodiment.

FIG. 6 is a block diagram illustrating components of an example machine able to read instructions from a machine-readable medium and execute them in one or more processors (or controllers) in accordance with one example embodiment. The instructions (e.g., program code) may correspond to the process, for example, described in FIG. 5. The instructions also may correspond to the components/modules carrying out the functionality disclosed in FIGS. 1-4.

Specifically, FIG. 6 shows a diagrammatic representation of an example form of a computer system 600. The computer system 600 can be used to execute instructions 624 (e.g., structured as program code or software) for causing the machine to perform any one or more of the methodologies (or processes) described herein, for example, in FIGS. 1-5. The machine may operate as a standalone device or a connected (e.g., networked) device that connects to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a smartphone, an internet of things (IoT) appliance, a network router, switch or bridge, or any machine capable of executing instructions 624 (sequential or otherwise) that specify actions to be taken by that machine. Further, while only a single machine is illustrated, the term "machine" shall also be taken to include any collection of machines that individually or jointly execute instructions 624 to perform any one or more of the methodologies discussed herein. In addition, it is noted that not all the components noted in FIG. 6 may be necessary for a machine to be configured to execute the systems and/or processes described within the disclosure.

The example computer system 600 includes one or more processing units (generally processor 602). The processor 602 is, for example, a central processing unit (CPU), a graphics processing unit (GPU), a digital signal processor (DSP), a controller, a state machine, one or more application specific integrated circuits (ASICs), one or more radio-frequency integrated circuits (RFICs), or any combination of these. The processor 602 may be similar to processor 200. The computer system 600 also includes a main memory 604. The computer system may include a storage unit 616. The processor 602, memory 604, and the storage unit 616 communicate via a bus 608.

In addition, the computer system 600 can include a static memory 606, a graphics display 610 (e.g., to drive a plasma display panel (PDP), a liquid crystal display (LCD), or a projector). The computer system 600 may also include alphanumeric input device 612 (e.g., a keyboard), a cursor control device 614 (e.g., a mouse, a trackball, a joystick, a motion sensor, or other pointing instrument), a signal generation device 618 (e.g., a speaker), and a network interface device 620, which also are configured to communicate via the bus 608.

The storage unit 616 includes a machine-readable medium 622 on which is stored instructions 624 (e.g., software) embodying any one or more of the methodologies or functions described herein. The instructions 624 may also reside, completely or at least partially, within the main memory 604 or within the processor 602 (e.g., within a processor's cache memory) during execution thereof by the computer system 600, the main memory 604 and the processor 602 also constituting machine-readable media. The instructions 624 may be transmitted or received over a network 626 via the network interface device 620.

While machine-readable medium 622 is shown in an example embodiment to be a single medium, the term "machine-readable medium" should be taken to include a single medium or multiple media (e.g., a centralized or distributed database, or associated caches and servers) able to store the instructions 624. The term "machine-readable medium" shall also be taken to include any medium that is capable of storing instructions 624 for execution by the machine and that cause the machine to perform any one or more of the methodologies disclosed herein. The term "machine-readable medium" includes, but not be limited to, data repositories in the form of solid-state memories, optical media, and magnetic media.

Additional Considerations

The disclosed configuration provides benefits and advantages that include, for example, anonymizing, indexing, or compressing data entries in database using hash structures such as bloom filters or hash tables. These benefits include the recovery of one or more hashed data entries under approved circumstances through a third party or by decryption by the holder of the associated private key. Additional benefits and advantages may include processing, by the hash structures, hash representations of data entries or relative attributes between data entries. Thus, in example use cases, these advantages may enable drug development, treatments, or medical research while enhancing protection of the privacy of sensitive data entries indexed in databases or from other data sources.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms, for example, as illustrated in FIGS. 1-2. Modules may constitute either software modules (e.g., code embodied on a machine-readable medium) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

The various operations of example methods described herein may be performed, at least partially, by one or more processors, e.g., processor 200 or processor 602, that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs)).

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for indexing data entries (e.g., for enhancing privacy, anonymization, or data compression) that may be executed through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A computer-implemented method comprising:
   receiving, by an indexing system from a client device, a selection of a plurality of data elements of a plurality of data entries;
   receiving a hash representation of the plurality of data entries generated using the selected plurality of data elements;
   transmitting the hash representation to a cascade of bloom filters of the indexing system, the cascade of bloom filters including a plurality of bloom filters and a terminal bloom filter, each bloom filter of the cascade of bloom filters including an array of n bits, wherein n is an integer value, the cascade of bloom filters mapping hash representations to positions in the arrays, each bloom filter of the plurality of bloom filters configured to:
      determine to pass the hash representation responsive to determining that the bloom filter previously filtered another instance of the hash representation, wherein the bloom filter returns false positives but not false negatives regarding matching an element to a set of elements, and
      transmit the hash representation to a subsequent bloom filter in the cascade of bloom filters for filtering or passing to another subsequent one of the bloom filters responsive to the determination to pass the hash representation; and
   wherein at least one bloom filter of the plurality of bloom filters transmits the hash representation to the terminal bloom filter;
   determining that the plurality of data elements is anonymized in a database responsive to a determination by the terminal bloom filter to pass the hash representation, wherein the terminal bloom filter outputs the plurality of data entries that satisfies a criteria for anonymization;
   indexing the plurality of data entries into the database responsive to the determination that the plurality of data elements is anonymized in the database; and
   transmitting a notification by the indexing system to the client device, the notification indicating that the plurality of data entries have been indexed into the database.

2. The computer-implemented method of claim 1, further comprising:
   receiving an additional hash representation of an additional plurality of data entries;
   transmitting the additional hash representation to the cascade of bloom filters; and
   determining not to index the additional plurality of data entries responsive to determining that one of the bloom filters of the cascade does not pass the additional hash representation.

3. The computer-implemented method of claim 1, wherein the plurality of data entries includes a first data entry and a second data entry describing a first event and a second event, respectively, the method further comprising:
   determining a relative attribute between the first data entry and the second data entry, wherein the relative attribute represents a temporal distance between timestamps of the first event and the second event, the hash representation generated using at least the relative attribute.

4. The computer-implemented method of claim 1, wherein the database includes a compressed version of the plurality of data entries after indexing the plurality of data entries into the database.

5. The computer-implemented method of claim 1, wherein the selected plurality of data elements indicates at least a geographical location and a disease diagnosis of one or more subjects.

6. The computer-implemented method of claim 1, wherein the cascade of bloom filters includes a series of at least eleven bloom filters.

7. The computer-implemented method of claim 1, wherein the criteria is associated with a threshold number of data entries describing a population of subjects having a same geographical location and disease diagnosis.

8. A non-transitory computer-readable storage medium comprising stored program code for indexing of data entries in an indexing system, the program code when executed by at least one processor causes the processor to:
   receive, from a client device, a selection of a plurality of data elements of a plurality of data entries;
   receive a hash representation of the plurality of data entries generated using the selected plurality of data elements;
   transmit the hash representation to a cascade of bloom filters of the indexing system, the cascade of bloom filters including a plurality of bloom filters and a terminal bloom filter, each bloom filter of the cascade of bloom filters including an array of n bits, wherein n is an integer value, the cascade of bloom filters mapping hash representations to positions in the arrays, each bloom filter of the plurality of bloom filters configured to:
      determine to pass the hash representation responsive to determining that the bloom filter previously filtered another instance of the hash representation, wherein the bloom filter returns false positives but not false negatives regarding matching an element to a set of elements, and transmit the hash representation to a subsequent bloom filter in the cascade of bloom filters for filtering or passing to another subsequent one of the bloom filters responsive to the determination to pass the hash representation; and wherein at least one bloom filter of the plurality of bloom filters transmits the hash representation to the terminal bloom filter;

determine that the plurality of data elements is anonymized in a database responsive to a determination by the terminal bloom filter to pass the hash representation, wherein the terminal bloom filter outputs the plurality of data entries that satisfies a criteria for anonymization;

index the plurality of data entries into the database responsive to the determination that the plurality of data elements is anonymized in the database; and transmit a notification by the indexing system to the client device, the notification indicating that the plurality of data entries have been indexed into the database.

9. The non-transitory computer-readable storage medium of claim 8, further comprising program code that when executed causes the processor to:

generate an additional hash representation of an additional plurality of data entries;

transmit the additional hash representation to the cascade of bloom filters; and determine not to index the additional plurality of data entries responsive to determining that one of the bloom filters of the cascade does not pass the additional hash representation.

10. The non-transitory computer-readable storage medium of claim 8, wherein the selected plurality of data elements indicates at least a geographical location and a disease diagnosis of one or more subjects.

11. The non-transitory computer-readable storage medium of claim 8, wherein the cascade of bloom filters includes a series of at least eleven bloom filters.

12. The non-transitory computer-readable storage medium of claim 8, further comprising program code that when executed causes the processor to:

determine a relative attribute between a first data entry and a second data entry of the plurality of data entries, the hash representation generated using at least the relative attribute.

13. The non-transitory computer-readable storage medium of claim 12, wherein the first data entry and the second data entry describe a first event and a second event, respectively, and wherein the relative attribute represents a temporal distance between timestamps of the first event and the second event.

14. The non-transitory computer-readable storage medium of claim 8, wherein the database includes a compressed version of the plurality of data entries after indexing the plurality of data entries into the database.

15. The non-transitory computer-readable storage medium of claim 8, wherein the criteria is associated with a threshold number of data entries describing a population of subjects having a same geographical location and disease diagnosis.

* * * * *